United States Patent [19]
Klein

[11] Patent Number: 5,593,442
[45] Date of Patent: Jan. 14, 1997

[54] RADIALLY EXPANSIBLE AND ARTICULATED VESSEL SCAFFOLD

[75] Inventor: Enrique J. Klein, Los Altos, Calif.

[73] Assignee: Localmed, Inc., Palo Alto, Calif.

[21] Appl. No.: 463,166

[22] Filed: Jun. 5, 1995

[51] Int. Cl.$^6$ ........................................ A61F 2/04
[52] U.S. Cl. ................... 623/12; 623/1; 606/194; 606/198
[58] Field of Search ................. 623/1, 11, 12; 606/108, 191, 194, 195, 198; 604/96, 104, 281

[56] References Cited

U.S. PATENT DOCUMENTS

| | | | |
|---|---|---|---|
| 4,776,337 | 10/1988 | Palmaz | 128/343 |
| 5,102,417 | 4/1992 | Palmaz | 606/195 |
| 5,104,404 | 4/1992 | Wolff | 623/1 |
| 5,135,536 | 8/1992 | Hillstead | 606/195 |
| 5,195,984 | 3/1993 | Schatz | 606/195 |
| 5,282,824 | 2/1994 | Gianturco | 606/198 |
| 5,354,308 | 10/1994 | Simon et al. | 606/198 |
| 5,449,373 | 9/1995 | Pinchasik et al. | 606/198 |

FOREIGN PATENT DOCUMENTS

| | | |
|---|---|---|
| 2079944 | 4/1993 | Canada . |
| 0481365A1 | 4/1992 | European Pat. Off. . |
| 0540290A2 | 5/1993 | European Pat. Off. . |
| 0662307 | 7/1995 | European Pat. Off. .......... A61F 2/06 |
| 9206734 | 4/1992 | WIPO .................... 606/194 |

*Primary Examiner*—Randy C. Shay
*Attorney, Agent, or Firm*—Townsend and Townsend and Crew LLP

[57] ABSTRACT

A radially expansible lumenal prosthesis comprises a plurality of body segments which are joined by universal articulation structures. Each universal articulation structure consists of a serpentine ring and two pairs of beam members. By joining adjacent body members to the serpentine ring using beam members, an articulated connection is provided while permitting radial expansion of all components. Optionally, linear elements within the body segment or segments may be protected and/or anchored by loop structures joined to or between longitudinal elements of the terminal body segments.

6 Claims, 5 Drawing Sheets

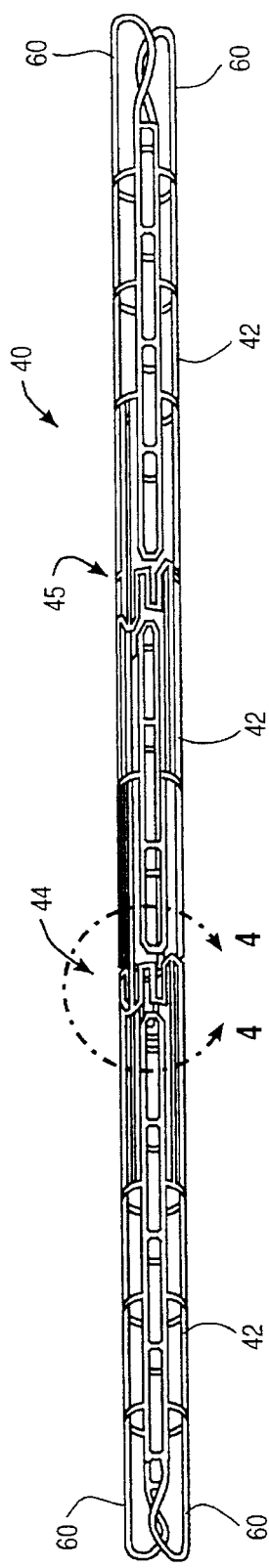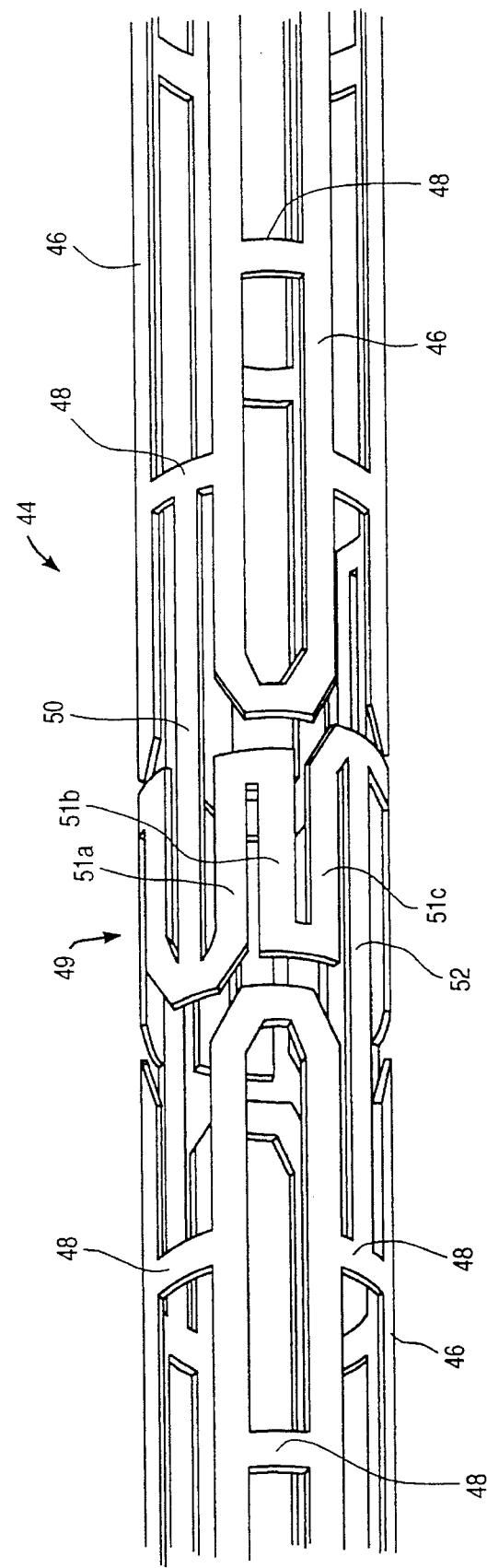
FIG. 3
FIG. 4A 5,593,442

RADIALLY EXPANSIBLE AND ARTICULATED VESSEL SCAFFOLD

BACKGROUND OF THE INVENTION

1. Field of the Invention

The present invention relates generally to the structure of radially expansible lumenal prostheses, including stents and grafts. More particularly, the present invention relates to the provision of articulation structures for the construction of flexible and pseudo-flexible prostheses and the provision of end structures for the construction of atraumatic prostheses.

Lumenal prostheses are provided for a variety of medical purposes. For example, lumenal stents can be placed in various body lumens, such as blood vessels, and the ureter, urethra, biliary tract, and gastrointestinal tract, for maintaining patency. Such stents are particularly useful for placement in pre-dilated atherosclerotic sites in blood vessels. Lumenal grafts can be placed in blood vessels to provide support in diseased regions, such as abdominal and other aneurysms.

Both stent and graft prostheses must meet certain mechanical criteria to function successfully. In particular, such prostheses should be at least partly flexible over their lengths so that they may be advanced through tortuous body lumens, such as the coronary vasculature. In addition, such prostheses must have sufficient mechanical strength, particularly hoop strength, in order to maintain lumen patency and/or mechanically augment the lumenal wall strength. The ability to meet both of these requirements is severely limited in the case of cylindrical endolumenal prostheses which are delivered in a radially constrained or collapsed configuration. Such prostheses must be radially expanded at a target site within the body lumen, so any adaptations which are intended to enhance flexibility or maintain strength must not interfere with the ability to radially expand.

Prior lumenal prostheses such as stents often have structures which present a substantial risk of injury as they are endolumenally delivered to and/or released at a target site within a patient body lumen. In particular, many vascular stents comprise a plurality of circumferentially spaced-apart cylindrical longitudinal elements which deform circumferentially as the stent is radially expanded. The Palmaz stent described in U.S. Pat. Nos. 5,102,417 and 4,776,337, is typical of such stents. The termini of the longitudinal elements of such stent structures present sharp, crown-like spikes which can injure or traumatize the blood vessel wall as the stent is delivered and/or radially expanded within the blood vessel.

For these reasons, it would be desirable to provide improved cylindrical lumenal prostheses and methods for their endolumenal placement, where the prostheses can flex in their radially constrained or collapsed configuration while they are being delivered to a target site within a body lumen. The prostheses will be radially expansible at the target location, and will preferably retain both their cylindrical configuration and flexibility after expansion. Such prostheses should further have sufficient hoop strength and other mechanical characteristics so that they may effectively function as stents in maintaining lumenal patency and/or grafts in enhancing lumenal wall strength. Such prostheses should also be provided with atraumatic termini in order to minimize the risk of lumenal injury as the prosthesis is delivered and/or radially expanded within the body lumen. Optionally, such atraumatic termini could also act as anchors for maintaining the prosthesis in the body lumen after expansion.

2. Description of the Background Art

Vascular stents comprising multiple segments joined by axial hinge structures are described in U.S. Pat. Nos. 5,195,984; 5,104,404; and 5,102,417 and European Patent Publication EP 540 290. Other stent structures are described in U.S. Pat. No. 5,282,824, European Patent Publication EP 481 365; and Canadian Patent Publication 2,079,944. U.S. Pat. No. 4,776,337 describes the Palmaz stent which consists of multiple longitudinal box elements joined to each other by short circumferentially oriented tabs.

SUMMARY OF THE INVENTION

The present invention provides improved prostheses and methods for their endolumenal placement within body lumens, particularly blood vessels. The prostheses may be in the form of stents, intended for maintaining lumenal patency, or may be in the form of grafts, intended for protecting or enhancing the strength of the lumenal wall. The prostheses of the present invention will be radially expansible, either by the application of an internal force to expand a non-resilient (usually malleable) prosthesis structure or by release of radial constraint from a resilient (self-expanding) prosthesis structure.

In a first aspect of the present invention, the prosthesis comprises a plurality of radially expansible, usually cylindrical, body segments. Consecutive body segments are joined by a universal articulation structure which consists of (a) a radially expansible serpentine ring and (b) two pairs of beam members. One beam member pair is disposed longitudinally on each side of the serpentine ring, and the articulation structure is completed by attaching each beam member pair to each of the consecutive body segments. The beam member pairs joined to each serpentine ring are rotationally offset by 90° to permit flexing (articulation) around two orthogonal axes. Thus, the articulation structure provides a "universal joint" that does not require any moving parts, only the flexing beam member pairs.

Preferably, the beam member pairs will be joined to the serpentine ring in a manner so that they will longitudinally overlap with each other and with both the body segments and the ring when the prosthesis is radially collapsed, compressed, or constricted. As the ring is radially expanded, the beam member pairs (attached to the same serpentine ring) will move longitudinally apart to increase the overall length between successive body segments. Such elongation is a particular advantage when the body segments are formed from structures which longitudinally shorten upon radial expansion, such as the longitudinal box elements characteristic of the Palmaz stents. That is, by longitudinally elongating the articulation structure, the shortening of the body segments can at least partially be offset to minimize shortening of the prosthesis.

In a second aspect of the present invention, a radially expansible prosthesis comprises a plurality of longitudinal elements, wherein said longitudinal elements move circumferentially apart (optionally deforming and axially shortening) as the body is radially expanded. Such a structure can be provided by a Palmaz stent, as described above. The present invention provides at least one atraumatic and/or self-anchoring end on such a prosthesis structure by incorporating loop elements disposed on or between at least some of the longitudinal elements. Preferably, the loop structures will be formed on both ends of the prosthesis. The loop structures are preferably formed as arcuate curved components between some of the circumferentially adjacent longitudinal elements, and act to both shield the otherwise traumatic ends of the longitudinal elements and as anchors which may be deflected outwardly into the lumenal wall after or during initial deployment.

Methods of the present invention comprise introducing any of the prostheses as described above to a target site within a body lumen. The prosthesis is then caused to radially expand after reaching the target site. Radial expansion can be effected either by applying an internal, expansive force to a malleable prosthesis or by releasing a self-expanding prosthesis from radial constraint.

BRIEF DESCRIPTION OF THE DRAWINGS

FIG. 1A is a schematic illustration of the device of FIG. 1, shown in a bent or flexed configuration.

FIG. 3 is a perspective view of a vascular stent constructed in accordance with the principles of the present invention.

FIG. 4A is a detailed view taken along line 4—4 of FIG. 3, illustrating the universal articulation structure of the stent in detail.

DESCRIPTION OF THE SPECIFIC EMBODIMENTS

Figure 1:
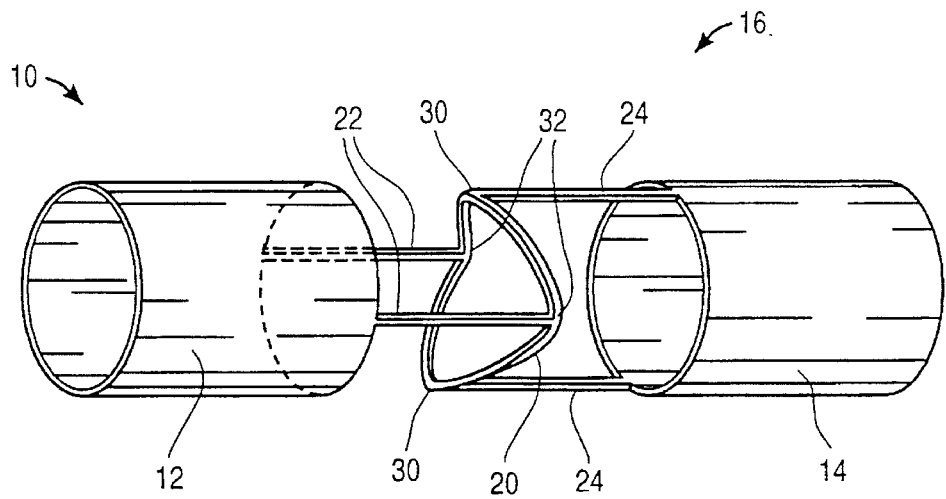
FIG. 1 is a schematic illustration of a radially expansible lumenal prosthesis having a pair of adjacent body segments joined by a universal articulation structure in accordance with the principles of the present invention, shown in its radially constrained or collapsed configuration.

The present invention provides devices and methods for the endolumenal placement of prostheses, particularly within the vascular system for the treatment of cardiovascular disease, such as vascular stenoses, dissections, aneurysms, and the like. The apparatus and methods, however, are also useful for placement in other body lumens, such as the ureter, urethra, biliary tract, gastrointestinal tract and the like, for the treatment of other conditions which may benefit from the introduction of a reinforcing or protective structure within the body lumen. The prostheses will be placed endolumenally. As used herein, "endolumenally" will mean placement by percutaneous or cutdown procedures, wherein the prosthesis is translumenally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the coronary arteries.

A lumenal prosthesis according to the present invention will comprise at least one radially expansible, usually cylindrical, body segment. By "radially expansible," it is meant that the body segment can be converted from a small diameter configuration (used for endolumenal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. As will be described below, the present invention provides atraumatic ends which are particularly useful for non-resilient prosthesis which are not protected by sheaths during delivery. Alternatively, the prosthesis can be self-expanding. Such self-expanding structures are provided by utilizing a resilient material, such as a stainless steel or superelastic alloy, and forming the body segment so that it possesses its desired, radially-expanded diameter when it is unconstrained, i.e. released from radially constraining forces a sheath. In order to remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well known in the art and do not comprise part of the present invention.

The dimensions of the lumenal prosthesis will depend on its intended use. Typically, the prosthesis will have a length in the range from 0.5 cm to 10 cm, usually being from about 0.8 cm to 5 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 30 mm, preferably being in the range from about 3 mm to 15 mm for vascular applications.

The articulated structure of the present invention is particularly advantageous since a single, long, flexible or pseudo-flexible prosthesis can be used instead of multiple, shorter prostheses (as is commonly done at present). In addition to flexibility, the structure of the present invention provides the advantage that the articulation structure axially elongates as it is radially expanded, thus at least partially offsetting axial shortening which may occur in the adjoining body segments. The flexibility is a particular advantage during initial delivery of the prosthesis when it will have to bend to pass through tortuous regions of a body lumen, such as a blood vessel. The flexibility remains, however, even after placement and radial expansion. The articulated structure provides a further advantage in that it expands to form a cylindrical structure between adjacent body segments. Many prior articulated prostheses rely on a single hinge member or other non-cylindrical structure which is unable to adequately support the lumenal wall between adjacent body segments.

The body segments may be formed from conventional materials used for body lumen stents and grafts, typically being formed from malleable metals, such as 300 series stainless steel, or from resilient metals, such as shape memory alloys, e.g. NiTi alloys, plated spring steel, and the like. It is possible that the body segments could be formed from combinations of these metals, or combinations of these types of metals and other non-metallic materials.

Exemplary structures for the body segments of the present invention is illustrated in U.S. Pat. Nos. 5,195,417; 5,102, 417; and 4,776,337, the full disclosures of which are incorporated herein by reference. These patents illustrate the basic structures characteristic of the Palmaz stent, which is presently being manufactured by Johnson and Johnson Interventional Systems. The Palmaz stent is characterized by a plurality of longitudinal cylindrical elements in the form of rectangular boxes expand into diamond-shaped patterns as the body segment is radially expanded. Preferably, circumferentially adjacent box elements are joined by short circumferentially oriented tab elements disposed in the center of the box elements.

The present invention provides improvements over the Palmaz stent in at least two different aspects. First, successive body segments of the type described by Palmaz, may be joined by universal articulation structures which permit bending in any direction. The articulation structures of the present invention are particularly useful with relatively rigid body cylindrical segments, particularly when those segments axially shorten upon radial expansion, as do the Palmaz-type segments.

The articulation structures of the present invention consist of (a) a radially expansible serpentine ring (which usually is cylindrical in both the compressed and expanded configurations) and (b) two pairs of beam members, with one beam member pair disposed longitudinally on each side (i.e., distal and proximal, of the serpentine ring. The beam member pairs are rotationally offset by 90°, thus forming a "universal joint" which permits bending between body segments resulting from transverse bending of the beam members. The articulation structure is also mechanically stable in both the radially compressed and radially expanded configuration, i.e. resistant to collapse and capable of maintaining its cylindrical configuration before and after expansion. Moreover, by joining the beam member pairs to the serpentine ring in a longitudinally overlapping pattern, the articulation can be formed to longitudinally elongate as the prosthesis is radially expanded. Such longitudinal elongation is desirable to offset the axial shortening of the body segments (which is characteristic of segments such as those described in the above-incorporated patents).

In addition to providing flexibility, the articulation structures of the present invention provide (a) adequate support or "scaffolding" between consecutive body segments to inhibit localized restenosis and (b) axial elongation upon radial expansion to at least partly offset axial shortening of the body segments. As particularly seen in FIG. 4B below, the serpentine ring retains a cylindrical "zig-zag" pattern even after radial expansion. Thus, the ring will continue to provide significant contact with and support of the inner wall of the body lumen. The axial elongation results from the attachment pattern of the beam members to the serpentine ring, where opposed beam member pairs move in opposite directions (thus increasing the overall length of the articulation structure) as the structure is radially expanded. In addition, the articulation structures can remain bent after deployment to allow the prosthesis to conform to a variety of lumenal shapes over long periods of time.

A second improvement over the Palmaz stent is provided by terminal loop structures which may be formed on or between the longitudinal elements of the prosthesis. Such loop elements preferably lie within the cylindrical volume defined by the body segments and articulation structures, as described in detail hereinbelow in connection with FIG. 5. While the prostheses of the present invention will preferably include both the universal articulation structure and the terminal loop structure, it will be appreciated that either of these aspects of the present invention may be employed by itself to provide an improved prosthesis.

Figure 2:
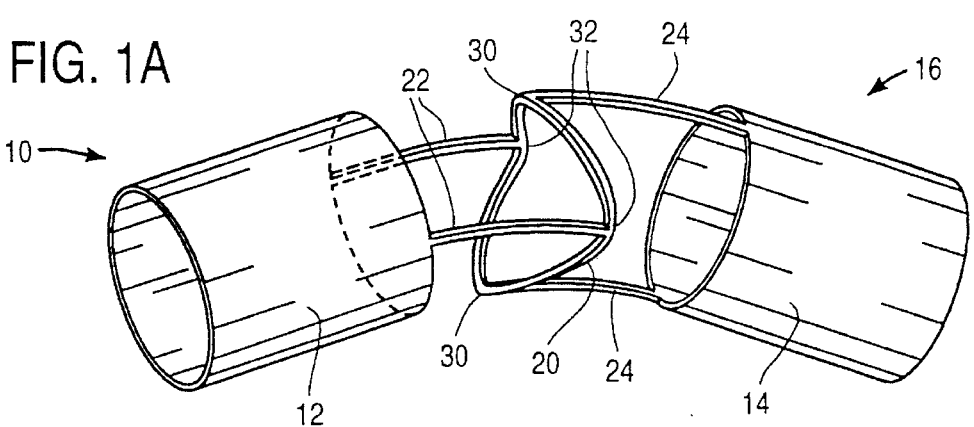
FIG. 2 is a schematic illustration of the device of FIG. 1, shown in its radially expanded configuration.
Figure 2:
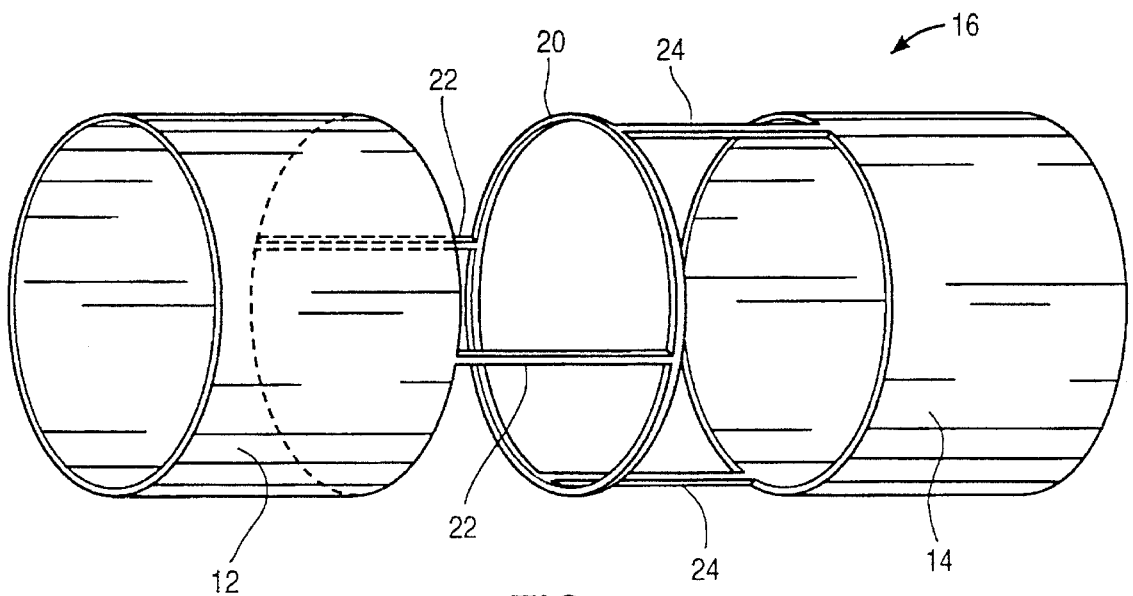

Referring now to FIGS. 1 and 2, a cylindrical radially expansible lumenal prosthesis 10 constructed in accordance with the principles of the present invention is illustrated schematically. The prosthesis 10 includes a first cylindrical body segment 12 and a second cylindrical body segment 14. The body segments will be radially expansible, as described above, but are illustrated as simple cylinders to facilitate explanation of a universal articulation structure 16 which joins the segments. The universal articulation structure comprises a serpentine ring 20, a first pair of beam members 22 joining the ring to the first body segment 12, and a second pair of beam members 24 joining the ring of the second body segment 14. The serpentine ring 20 is formed as a single, elongate element which is patterned in a serpentine or "undulating" configuration. Conveniently, the entire prosthesis, including the body segments and the articulation structure(s) can be formed by laser cutting, electromachining, and/or chemical etching of solid tubular (i.e., cylindrical) starting materials. Such techniques are well described in the technical and patent literature.

In the radially compressed configuration of FIG. 1, the serpentine ring 20 will have a generally cylindrical outer periphery, but will turn back and forth in the longitudinal direction. In the schematic embodiment of FIGS. 1 and 2, the ring 20 includes only four segments which turn back and forth in a simple direction-reversing pattern. The segments have two points 30 which lie closest to the first body segment 12 and two points 32 which lie closest to the second body segment 14. The first pair of beam members 22 extend from the first body segment to the points 32, while the second pair of beam members 24 extend from the second body segment to the first points 30. Thus, in the collapsed cylindrical configuration of FIG. 1, the first beam member pair 22 and second beam member pair 24 are longitudinally partially overlapped. When expanded, the beam members 22 and 24 move longitudinally apart as the serpentine ring 20 radially expands. Thus, the longitudinal distance between first body segment 12 and second body segment 14 will increase. As discussed above, such increase is desirable since it can be made to at least partly offset a longitudinal shortening of the body segments 12 and 14. The ability of the lumenal prosthesis 10 to flex in its compressed configuration is shown in FIG. 1A. The prosthesis 10 will retain a similar ability to flex in its expanded configuration (not shown).

Figure 4B:
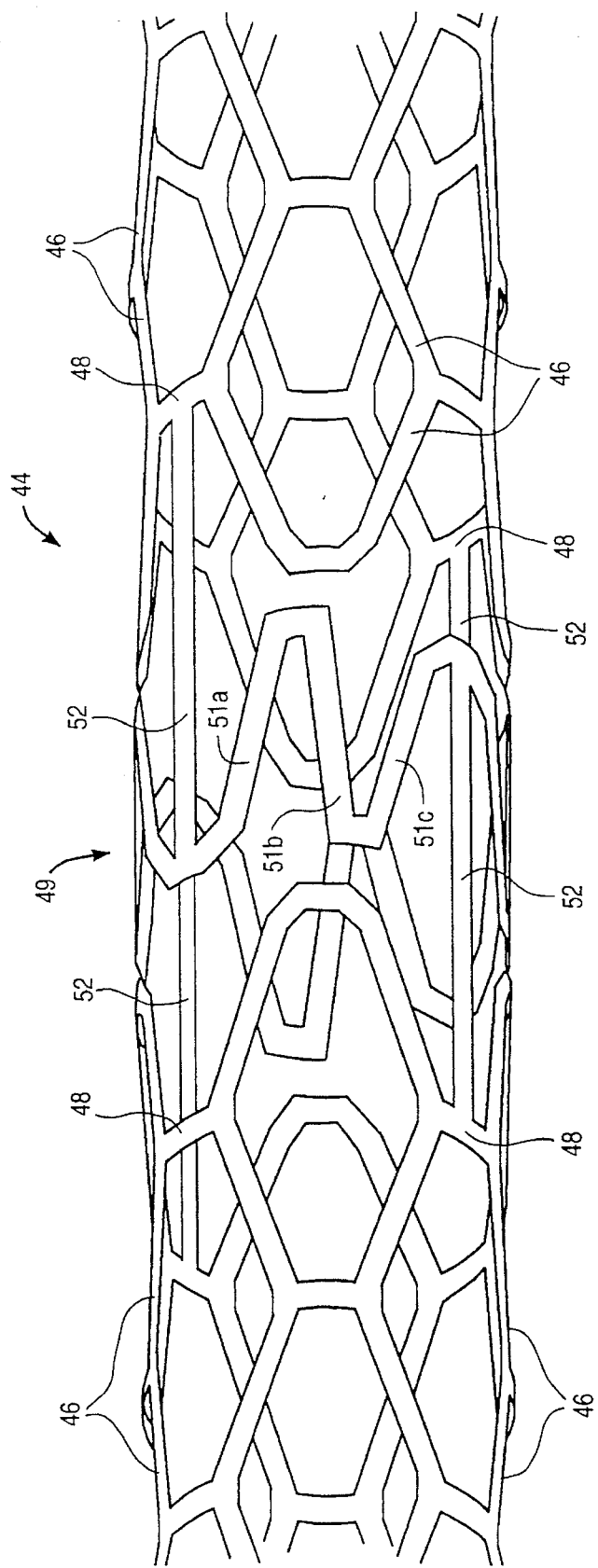
FIG. 4B is a view similar to FIG. 4A, except that the articulation structure is radially expanded.

A preferred vascular stent structure 40 is illustrated in FIGS. 3, 4A, and 4B. The stent structure 40 comprises three radially expansible body sections 42 joined by two universal articulation structures 44 and 45, with structure 44 being illustrated in detail in FIG. 4A. The body segments each include four linear, box structures 46 (each of which include three or four adjacent rectangular boxes) which are circumferentially joined by tabs 48. The articulation structure comprises a cylindrical serpentine ring 49 having three linear elements 51a, b, and c between adjacent beam members 50 and 52, with beam members 50 and 52 belonging to different beam member pairs. Beam members 50 and 52 extend from the serpentine ring 49 to selected tab members 48. It will be appreciated that the serpentine ring 49 will radially expand as the body members 42 are expanded in a conventional manner, e.g. by application of an internal balloon force. The final shape of the ring 49 will generally be cylindrical, although it will also be conformable to non-cylindrical cross-section lumens. Additionally, the beam members 50 and 52 will move longitudinally apart in a manner analogous to that described in connection with FIGS. 1 and 2. Thus, the linear elongation of the articulation structure will at least partially offset the longitudinal shortening of the body segments 42. The articulation structure 44 is shown in a radially expanded configuration in FIG. 4B.

The articulation structure can flex via the beam member pairs in both the compressed and expanded configurations of the stent 40.

Figure 5:
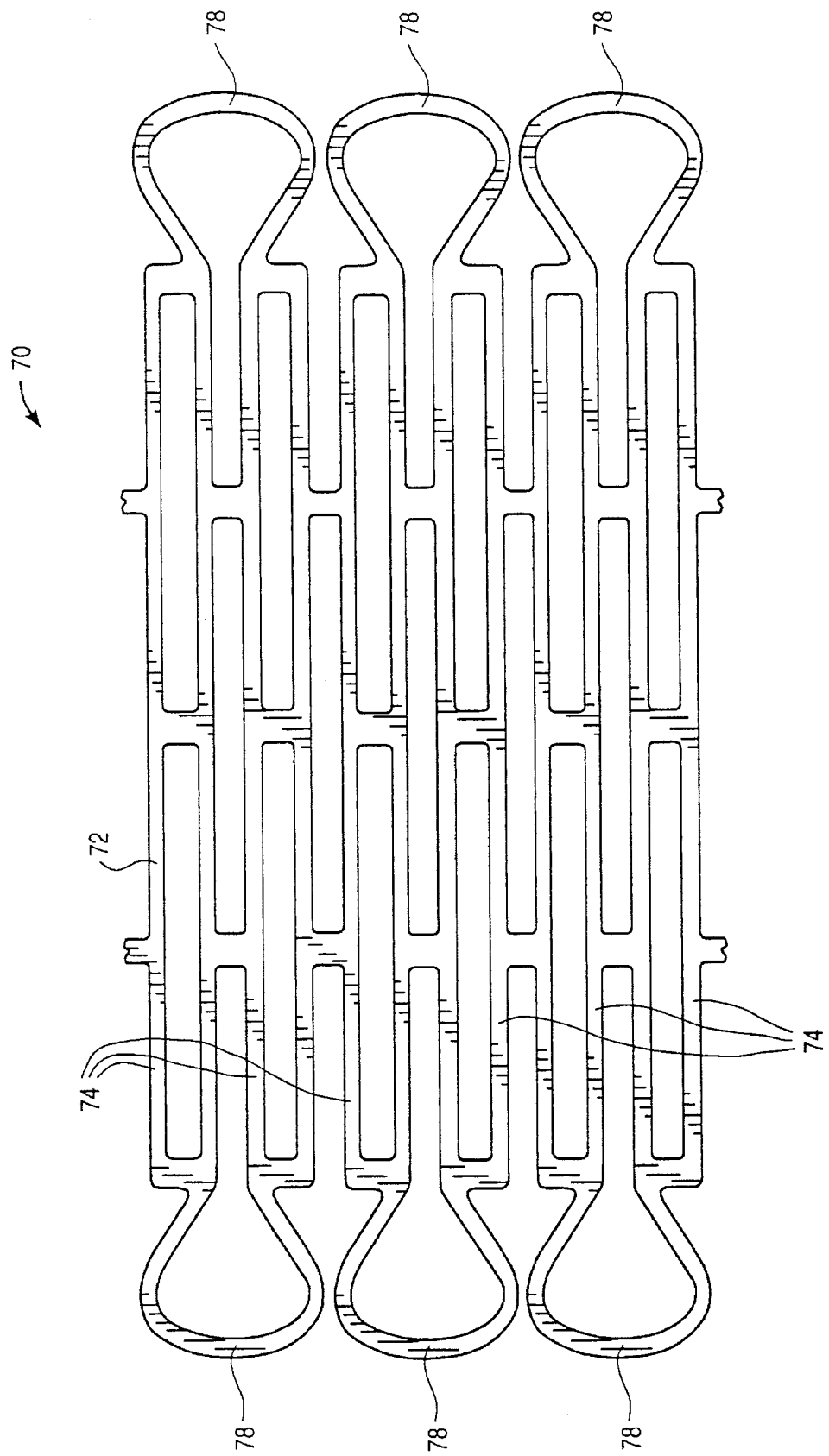
FIG. 5 is a "rolled out" view of a vascular stent having atraumatic ends, constructed in accordance with the principles of the present invention.
Figure 5A:
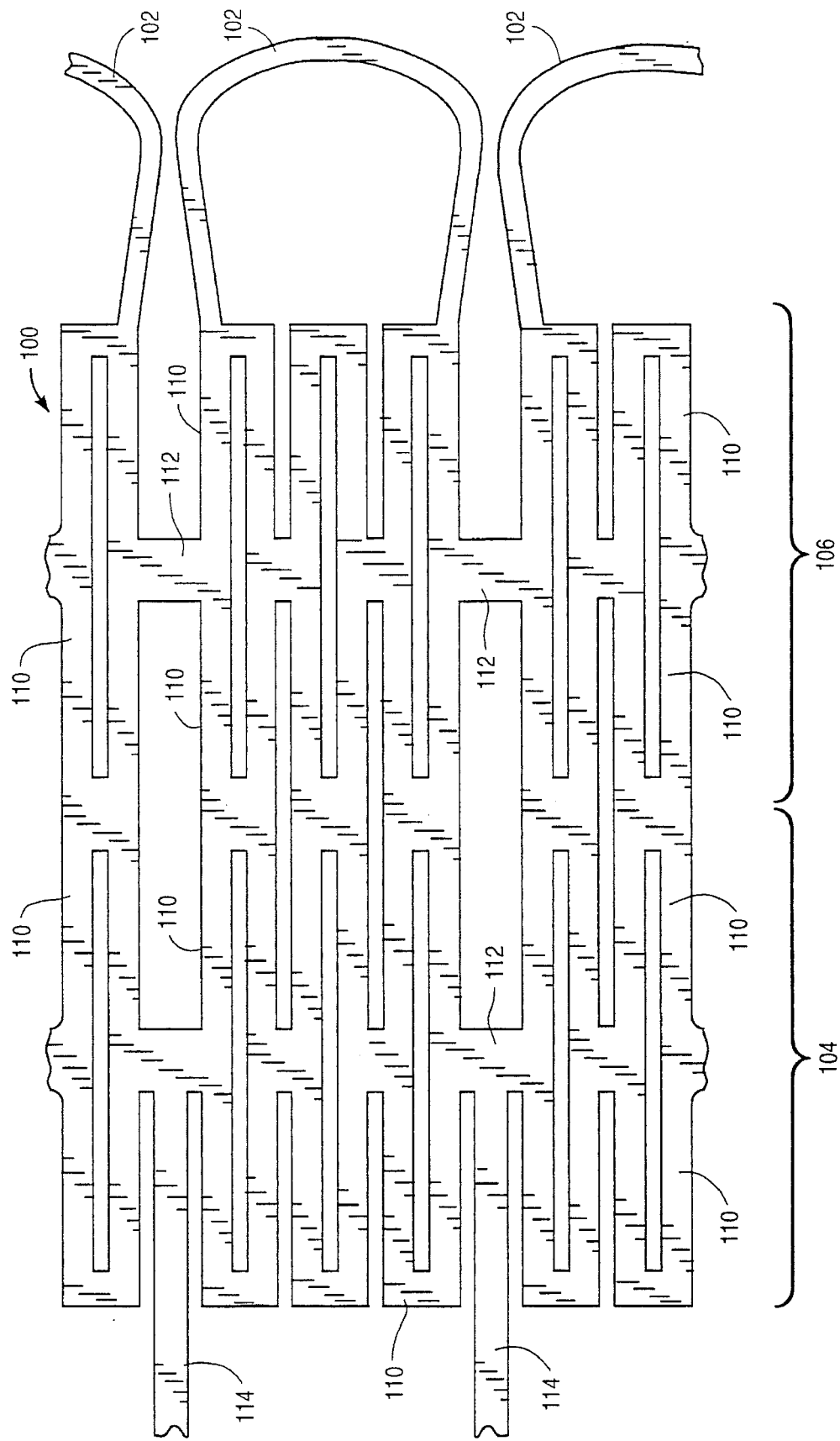
FIG. 5A illustrates a vascular stent having an alternative atraumatic end structure.

The vascular stent 40 also includes loop structures 60 which join pairs of longitudinal elements 46 at each end of the stent 40. It will be appreciated that the loop structures 60 can be utilized with stents which do not include articulation structures, as illustrated in FIGS. 5 and 5A. FIG. 5 is a "rolled-out" pattern of a cylindrical vascular stent 70 comprising a single body segment 72. The body segment 72 comprises six circumferentially adjacent box elements 74, where three loop structures 78 are provided on each end of the body segment to join pairs of adjacent box elements 74. The loop elements provide atraumatic ends for the graft and are sufficiently long so that they can hold the ends of pairs of adjacent linear members together as the stent is radially expanded while maintaining an arcuate profile that matches the circular circumference of the prosthesis. The loop structures 60 can alternatively or simultaneously be deployed as "anchors" by over expanding the distal ends of the prosthesis so that the loop structures will engage the lumenal tissue, thus holding the prosthesis in place. Such over expansion can be achieved with balloon deployment and would be particularly effective with malleable structures which can be readily "set" by such expansion.

A partial view of an alternative stent 100 having end loops 102 is partly illustrated in FIG. 5A. The view is "rolled out" and depicts one complete cylindrical radially expansible body segment consisting of two longitudinally adjacent rows of linear box structures 104 and 106, with each row comprising six expansible box structures 110 arranged circumferentially and joined by tabs 112. Selected tabs may be joined by one pair of beam members 114 to provide for articulation structures as described above (the serpentine ring structure is not illustrated in FIG. 5A). The stent 100 differs from stent 40 in that each loop structure 102 is joined to circumferentially spaced-apart ends of the same row of structures 106, rather than circumferentially adjacent sections.

Although the foregoing invention has been described in some detail by way of illustration and example, for purposes of clarity of understanding, it will be obvious that certain changes and modifications may be practiced within the scope of the appended claims.

What is claimed is:

1. A radially expansible lumenal prosthesis comprising:

a plurality of radially expansible body segments, wherein the expansible body segments each comprise a plurality of box elements which expand into arcuate, diamond-shaped elements as the body segment is expanded and wherein circumferentially adjacent box elements are joined to each other near their longitudinal centers by circumferentially oriented tabs, and wherein said beam members are joined to tabs which are offset from each other by 90°; and a universal articulation structure between each pair of consecutive body segments, wherein said articulation structure consists of (a) a radially expansible serpentine ring, wherein the serpentine ring of the universal articulation structure is configured so that the ends of the beam member pairs which are attached to the serpentine ring longitudinally overlap when said ring is radially constricted and move axially apart as the ring is radially expanded and (b) two pairs of beam members, wherein said beam member pairs are rotationally offset by 90° and wherein beam member pairs are disposed longitudinally on each side of the ring and each beam member pair is attached to one of said consecutive body segments.

2. A radially expansible lumenal prosthesis as in claim 1, wherein the serpentine ring includes at least three segments joined in a reversing pattern between each beam member.

3. A radially expansible lumenal prosthesis as in claim 1, further comprising loop elements joining pairs of adjacent ends of at least some of the longitudinal elements.

4. A method for reinforcing the wall of a body lumen, said method comprising introducing a prosthesis as set forth in claim 1 to a target site within the body lumen, wherein said prosthesis is radially expanded after reaching said target site.

5. A method as in claim 4, wherein the prosthesis is caused to expand by applying an expansive force within the prosthesis.

6. A method as in claim 4, wherein the prosthesis is permitted to expand by releasing the prosthesis from radial constraint at said target site.

* * * * *